United States Patent [19]

Wolf

[11] Patent Number: 5,785,524
[45] Date of Patent: Jul. 28, 1998

[54] SECURING DEVICE FOR TOOTH IMPLANTS

[75] Inventor: Manfred Wolf, Leinfelden-Echterdingen, Germany

[73] Assignee: Metaux Precieux SA Metalor, Switzerland

[21] Appl. No.: 817,716

[22] PCT Filed: Sep. 28, 1995

[86] PCT No.: PCT/EP95/03839

§ 371 Date: Mar. 27, 1997

§ 102(e) Date: Mar. 27, 1997

[87] PCT Pub. No.: WO96/10964

PCT Pub. Date: Apr. 18, 1996

[30] Foreign Application Priority Data

Oct. 6, 1994 [DE] Germany ............ 44 35 694.3
Sep. 14, 1995 [DE] Germany ............ 195 34 169.4

[51] Int. Cl.6 .................................. A61C 8/00
[52] U.S. Cl. ............................ 433/173; 433/172
[58] Field of Search ...................... 433/172, 173

[56] References Cited

U.S. PATENT DOCUMENTS 5,302,126 4/1994 Wimmer et al. .................. 433/173
5,447,434 9/1995 Shaw ................................. 433/173

FOREIGN PATENT DOCUMENTS 1313597 2/1993 Canada .
8905497 9/1989 Germany .

*Primary Examiner*—John J. Wilson
*Attorney, Agent, or Firm*—Dick and Harris

[57] ABSTRACT

The invention relates to a accusing device (11) for the durable, hard-wearing and reliably scaled arrangement of tooth implants (31). It has an implant body (10) insertable into a prepared drilling in the jawbone and having an axial threaded blind hole (14) for the insertion of a securing screw (16) to accept a crown or bridge body (31). On the annular face (18 or 28) of the screw head (26) and the implant body (10) there is a concentric annular sealing edge (19 or 30) which, when the crown or bridge body (31) is clamped, enters corresponding annular surfaces thereon and thus provides the required seal.

18 Claims, 2 Drawing Sheets

SECURING DEVICE FOR TOOTH IMPLANTS

BACKGROUND OF INVENTION

The invention concerns a securing device for dental implants.

A securing device of this type is known from Canadian Patent 1,313,597 (FIG. 6).

With this design, the screw connection for securing a crown or bridge on the implant body is designed in two parts. One part forms a screw that can be screwed with its threaded shaft into a central threaded hole drilled in the implant body and it also has a bent thread-free cylindrical shaft part onto which a sleeve-like socket can be placed to secure it. With a peripheral face part that tapers conically toward the bottom, the cylindrical shaft part is supported on a complementary inside ring-shaped shoulder of the securing socket, so the socket and the implant body can be secured together axially.

Between the two parts there is a ring gasket whose lower ring face receives a concentric ring-shaped sealing edge that is provided on the upper ring face of the implant body so as to form a seal.

Another seal is provided in the form of a ring gasket that is inserted in a peripheral groove of the cylindrical shaft part of the connecting screw and is supported on the inside circumference of the sleeve-like securing socket.

The other part of the screw connection is formed by an anchoring screw that can be screwed with its threaded shaft into a central threaded hole in the cylindrical shaft part of the connecting screw. The anchoring screw serves to axially secure a receptacle part for a dental prosthesis in the form of a crown or a bridge, which also forms the upper cap part of the sleeve-like securing socket.

Therefore, the anchoring screw has a screw head that tapers conically toward the lower end and is supported on the inside peripheral part of a central cylindrical drilling in the receptacle part with a matching conical taper.

The receptacle part in turn sits securely in a crown or bridge that can be secured on the socket base by tightening the anchoring screw.

The arrangement of the sealing devices explained here (O ring; ring gasket and sealing edge) prevents the seepage of oral fluids that might lead to an infection into the implant body.

The type of seal described here is formed by the multi-part and thus expensive design of this securing device.

SUMMARY OF INVENTION

The object of this invention is to provide a securing device that will assure a tight reliable seating of crowns or bridges on post-like implant bodies without requiring any additional special sealing elements.

Due to the fact that the ring-shaped faces of the screw head and the implant body are each provided with a ring-shaped sealing edge, a form-fitting mutual meshing of these ring-shaped faces with a crown or bridge is achieved because when the securing screw is tightened it produces a high surface pressure leading to plastic deformation of the ring-shaped face of the crown or bridge supported on the respective sealing edge. This levels out the pits and cavities remaining between the ring-shaped faces that are to be tightened to each other. Accordingly, this yields a connection of the parts joined that remains absolutely tight over a period of time.

This invention makes it possible to attach a crown or a bridge directly to the implant body without having to use any additional sealing agents and thus it greatly simplifies the overall design.

German Utility Patent 8,905,497.0 has already disclosed a securing device for dental implants having a shell-like prosthesis anchoring device that can be screwed onto an implant body to be implanted in the jawbone. On its lower ring-shaped face which has a threaded shaft, the prosthesis anchoring device has a concentric collar with a peripheral face that tapers conically toward the outside.

When the anchoring device is screwed in place, however, it does not sit on an inside ring-shaped shoulder of the crown or bridge as in the invention but instead it rests on the implant body itself.

The ring-shaped sealing edges provided according to this invention can be designed as part of the corresponding part by turning it on a lathe or by some other suitable method.

A preferred embodiment of the sealing edges is disclosed. Structure is also provided to promote the bonding of the material can be implemented on the end faces of the sealing edges with regard to the plastic deformation of the material to be accomplished.

It is also favorable if a strength gradient is provided with regard to the desired plastic deformation of the material with respect to the parts to be joined together.

In another advantageous embodiment of the invention, the securing screw has features to maintain a permanent seal.

Such a design of the securing screw makes it possible to achieve a great increase in its potential axial elasticity, which results in an increase in edge pressure of the meshed threads of the threaded shaft of the securing screw and the inside thread of the implant body and helps to maintain this pressure.

Depending on the structural height of the implant, it is advisable to design the length of the thread-free part of the shaft of the securing screw and the diameter of the screw head and provide a shaft thread according to the particular details described herein.

The pairing of materials between the securing screw and the bridge or crown and/or the implant body may be either lubricated or not lubricated. If lubricated, a significant increase in axial gripping force by minimizing the friction acting between the flanks of the thread.

The securing screw in the embodiment claimed here can be used to equal advantage for implants with a design that is bent or coaxial with the implant bodies.

BRIEF DESCRIPTION OF THE DRAWINGS

The figures illustrate one embodiment of a securing device according to this invention, where they show the following.

BEST MODE FOR CARRYING-OUT THE INVENTION

Figures 1, 2:
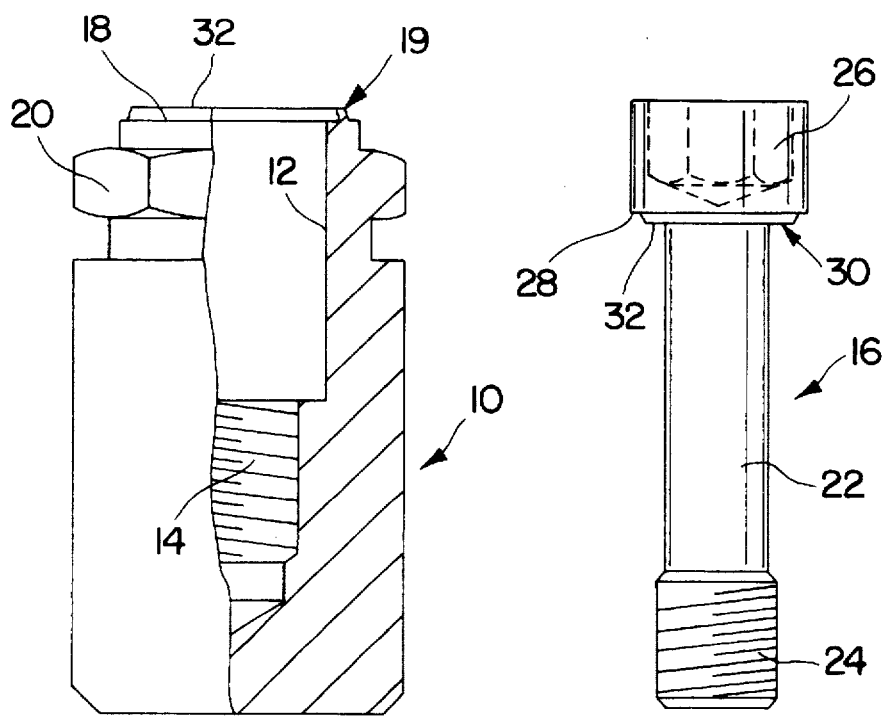
FIG. 1: shows the implant body of the securing device, shown partially in a longitudinal sectional view.
FIG. 2: shows the securing screw that can be screwed into the implant body for mutually securing the implant body and the crown or bridge, shown in preferred dimensions.

The implant body of the securing device 11 is designated as a whole as 10 in FIG. 1 and is designed as a circular cylinder in cross section. It has an axial blind hole 12 with an inside thread 14 cut in the area of the base of the blind hole for screwing in the securing screw 16 illustrated in FIG. 2. With the help of this screw, a conventional crown such as that illustrated in FIG. 6 can be secured to the upper ring-shaped face 18 of implant body 10, for example. A ring-shaped sealing edge 19 is provided concentrically on the ring-shaped face 18 of the implant body 10.

A hexagonal shape molded on the periphery in the area of ring-shaped face 18 is labeled as 20 and serves to secure the implant structures to prevent further rotation.

The thread-free shaft part 22 of the securing screw 16 is several times longer than its threaded shaft 24, which preferably has an M2 thread. The height of screw head 26 corresponds approximately to the diameter of shaft part 22.

Figure 6:
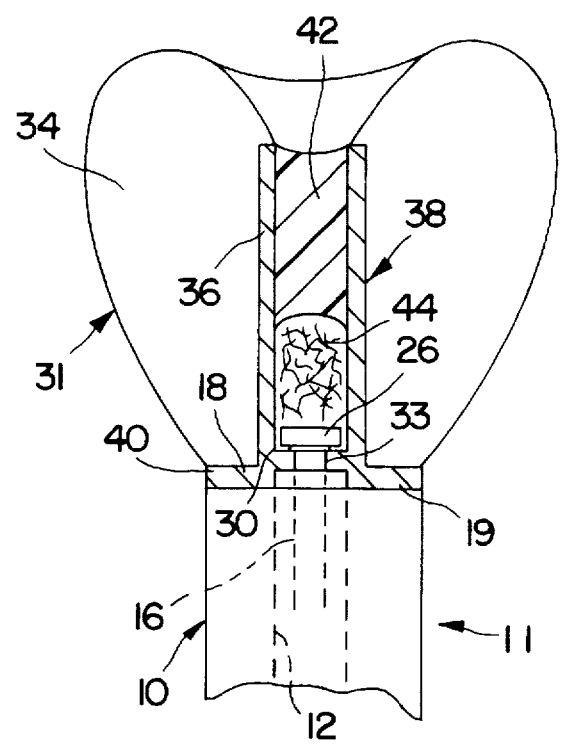
FIG. 6: shows a longitudinal section through a securing device holding a dental crown; shown in a shortened diagram.

With a ring-shaped sealing edge 30 attached concentrically to the ring-shaped face 28 of the screw head 26, the latter is supported on a corresponding inside ring-shaped shoulder 33 when the crown or bridge body 31 is tightened in place (see FIG. 6).

Figure 3:
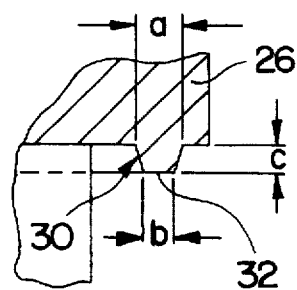
FIG. 3: shows a detail on a larger scale than FIG. 2, represented by a dash-dot circle.

According to FIG. 3, the sealing edges 19 and 30 preferably have a trapezoidal cross section with the following preferred dimensions:

Base width a: 0.10 mm

Width of flat ring-shaped face 32: 0.04 mm

Height of sealing edge c: 0.05 mm

Figures 4, 5:
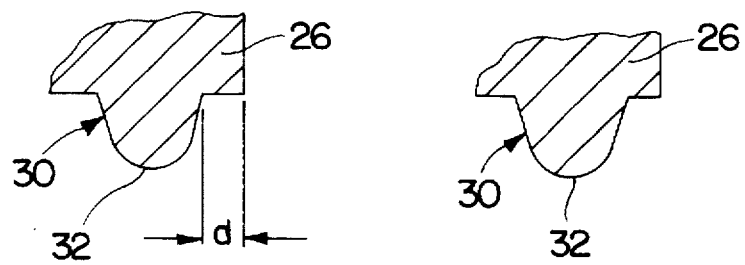
FIGS. 4 and 5: each show a cross section through variants of the sealing edge, where these also apply to the sealing edge of the implant body.

Radial distance d of sealing edge 30 from the outside periphery of screw head 26 or the implant body (FIG. 4): 0.05 mm It should be pointed out here that the diagrams of the sealing edges 19 and 30 according to FIGS. 3–5 do not correspond to the precise dimensions given here.

Although the ring-shaped face 32 of sealing edges 19 and 30 according to FIGS. 2 and 3 is designed to be flat, the displacement of material along the inside ring-shaped shoulder 33 of a crown or bridge that takes place under the influence of the tightening force in effect when tightening the securing screw 16 can be further promoted by the fact that the two boundary zones of ring-shaped faces 32 of sealing edges 19 and 30 are rounded, as illustrated in FIG. 4, and ring-shaped faces 32 are themselves designed with a slight convex curvature or, as shown in FIG. 5, with an at least approximately curved shape in cross section.

The securing screw preferably has the following specifications:

Length of threaded shaft 24: 1.60 mm

Pitch of the shaft thread: 0.40 mm

Length of thread-free shaft part 22: 5.00 mm

Diameter of thread-free shaft part: 1.50 mm

Height of the screw head 26: 1.50 mm

Outside diameter of the screw head 26: 2.50 mm

Inside diameter of the screw head: 2.10 mm

Flank diameter of the thread: 1.74 mm

Core diameter of the thread: 1.50 mm

Stress cross section of the thread-free part 22 of the shaft: 1.77 mm$^2$

Interfacial pressure: 1000 N/mm$^2$

Material of the securing screw 16: Ti6 Al 4V

Material number: 3.7165

Yield point: 1050 N/mm$^2$

Tensile strength: 1140 N/mm$^2$

Modulus of elasticity: 106,000 N/mm$^2$

Elongation at break: 15%

Reduction of area 40%

Endurance at 1,000,000 load cycles: ±230 N/mm$^2$

Assembly torque of securing screw 16: 30 Ncm

Securing screw 16 which conforms to these specifications is characterized by appropriate bending softness, a great axial elongation length and accordingly a settling loss which turns out to be negligible if a proper tensile stress that can be produced by the stated assembly torque is selected for mutual tightening of implant body 10 and a crown or bridge body 31 and thus the crown or bridge remains at tightly seated without being subject to any external influence.

As FIG. 6 shows, the crown body 31 includes a tooth body 34 made of ceramic, for example, and applied to a structural shell 36 of a crown support 38.

When crown body 31 is tightened onto implant body 10, structural shell 36 is at first supported with a lower outside flange 40 on sealing edge 19 of the upper ring-shaped face 18 of implant body 10, and screw head 26 of securing screw 16 rests with its sealing edge 30 on the inside ring-shaped shoulder 33 of structural shell 36.

The tension forces acting axially here cause the sealing edges 19, 30 to cut into the ring-shaped face of outside flange 40 or inside ring-shaped shoulder 33 until the ring-shaped faces that face each other are in contact. This is made possible by the fact that the crown support 38 is preferably made of gold and therefore there is a strength gradient between this part and the parts 10 and 16 that are made of titanium.

Sealing edges 19, 30 guarantee a satisfactory radial seal with respect to axial blind hole 12 of implant body 10.

Structural shell 36 is also sealed by a plastic filling 42, where a pellet 44 of foam is introduced between the filling and screw head 26 of the securing screw 16 to keep the internal polygonal shape of screw head 26 free of plastic so that crown 31 can be removed from implant body 10 at any time.

I claim:

1. A securing device for dental implants, with a securing screw (16) having a threaded shaft (24); and a post-like implant body (10) that can be inserted into a prepared drilling in the jawbone, the implant body having an axial blind hole thread (14) for inserting the threaded shaft (24) of the securing screw (16) to mount a crown or a bridge (31), which crown or bridge (31) is provided with an inside ring-shaped shoulder (33), and for securing the crown or bridge (31) on the implant body (10) the implant body further having a ring-shaped face (18), with a first ring-shaped sealing edge (19) provided on the ring-shaped face (18) facing the crown or the bridge (31); the securing screw (16) having a screw head (26) having a ring-shaped face 28 that engages the inside ring-shaped shoulder (33) of the crown or the bridge (31) characterized in that a second, opposing ring-shaped sealing edge (30) provided on the ring-shaped face (28) of the screw head (26) of the securing screw (16), and the ring-shaped sealing edges (19, 30) each directly engage the ring-shaped shoulder (33) on the structure (38) of the crown or bridge (31), the material of at least the implant body and the screw being harder than the material of the inside ring-shaped shoulder of the crown or bridge, each of the sealing edges extending from its respective face, so that upon positioning of the crown or bridge on the structure (38) and tightening down of the screw, the inside ring-shaped shoulder of the crown or bridge becomes axially engaged between the sealing edges, and the sealing edges press into opposed surfaces of the inside ring-shaped shoulder, causing plastic deformation thereof to form a seal.

2. Securing device according to claim 1, characterized by a trapezoidal cross section of the sealing edges (19, 30).

3. Securing device according to claim 2, characterized by the following dimensions of the trapezoidal sealing edges (19, 30), as seen in cross section:

base width a: 0.10 mm, width of flat ring-shaped face b: 0.04 mm, height of sealing edge c: 0.05 mm, radial distance d of sealing edges (19 or 30) from the outside perimeter of the part (10 or 16) carrying them: 0.05 mm.

4. Securing device according to claim 3, characterized by rounded inside and outside ring-shaped edges of the ring-shaped face (32) of the sealing edges (19, 30).

5. Securing device according to claim 3, characterized by a ring-shaped face (32) of the sealing edges (19, 30) with a convex curvature in cross section.

6. Securing device according to claim 1, characterized by a greater material strength of the part (10 or 16) carrying the sealing edges (19, 30) in comparison with the strength of the crown or bridge to be attached to it.

7. Securing device according to claim 1, characterized by the following features:

a) the length of the threaded shaft (24) of the securing screw (16) is between 1.00 mm and 2.00 mm;

b) the pitch of the shaft thread is between 0.2 mm and 0.6 mm;

c) the thread-free part (22) of the shaft has a diameter between 1.00 mm and 2.00 mm;

d) the length of the thread-free shaft part (22) is greater than the maximum length of the threaded shaft (24);

e) the height of the screw head (26) is between 1.00 mm and 3.0 mm.

8. The securing device according to claim 7, wherein the length of the threaded shaft (24) is 1.60 mm.

9. The securing device according to claim 7, wherein the pitch of the shaft thread is 0.4 mm.

10. The securing device according to claim 7, wherein the thread-free part (22) of the shaft has a diameter of 1.50 mm.

11. The securing device according to claim 7, wherein the height of the screw head (26) is 1.5 mm.

12. Securing device according to claim 1, characterized by a length of the thread-free shaft part (22) between 3.50 mm and 14.00 mm, preferably 5.00 mm.

13. The securing device according to claim 12, wherein the length of the thread-free shaft part (22) is 5.00 mm.

14. Securing device according to claim 1, characterized by a screw head diameter between 2.00 mm and 3.00 mm, preferably 2.50 mm.

15. Securing device according to claim 1, characterized by an M2 thread (24).

16. The securing device according to claim 1 wherein the sealing edges have a substantially trapezoidal configuration in cross-section.

17. The securing device according to claim 1 wherein the sealing edges are substantially concentric relative to one another.

18. A securing device for dental implants, for use in combination with a crown or bridge body, having a crown support having an inside ring-shaped shoulder with two axially opposed faces, and a bore extending axially through the crown support, the securing device comprising:

an implant body, having an axially extending blind bore therein, a portion of the bore being internally threaded, the implant body further having an annular face surrounding the opening of the blind bore, an axially extending sealing ridge emanating from the annular face and positioned to axially engage one of the axially opposed faces of a crown support of a crown or bridge body, when a crown or bridge body is mounted onto the securing device;

a screw, having a shaft with threaded and non-threaded portions and a screw head, an annular face on the screw head, an axially extending sealing ridge emanating from the annular face of the screw head and positioned to axially engage the other of the axially opposed faces of a crown support of a crown or bridge body, when a crown or bridge body is mounted onto the securing device;

the implant body and the screw being fabricated from a material which is harder than the material from which the crown support of a crown or bridge body is fabricated.

* * * * *